United States Patent
Cooklev

(10) Patent No.: US 6,359,998 B1
(45) Date of Patent: Mar. 19, 2002

(54) METHOD AND APPARATUS FOR WAVELET-BASED DIGITAL WATERMARKING

(75) Inventor: Todor Cooklev, Salt Lake City, UT (US)

(73) Assignee: 3Com Corporation, Santa Clara, CA (US)

( * ) Notice: Subject to any disclaimer, the term of this patent is extended or adjusted under 35 U.S.C. 154(b) by 0 days.

(21) Appl. No.: 09/065,815

(22) Filed: Apr. 23, 1998

(51) Int. Cl.$^7$ ................................................. G06K 9/00
(52) U.S. Cl. ...................................... 382/100; 382/248
(58) Field of Search ................................ 382/100, 101, 382/118, 119, 120, 212, 232, 248, 249, 250, 276, 280, 284, 293, 296; 380/54, 210, 252, 287; 713/176

(56) References Cited

U.S. PATENT DOCUMENTS

| | | | |
|---|---|---|---|
| 4,405,829 A | * 9/1983 | Rivest et al. | 178/22 |
| 5,721,788 A | * 2/1998 | Powell et al. | 382/100 |
| 5,745,604 A | * 4/1998 | Rhoads | 382/232 |
| 5,809,160 A | * 9/1998 | Powell et al. | 382/100 |
| 5,889,868 A | * 3/1999 | Moskowitz et al. | 380/51 |
| 5,905,819 A | * 5/1999 | Daly | 382/284 |
| 5,915,027 A | * 6/1999 | Cox et al. | 380/54 |
| 5,930,369 A | * 7/1999 | Cox et al. | 380/54 |
| 5,930,377 A | * 7/1999 | Powell et al. | 382/100 |
| 5,946,103 A | * 8/1999 | Curry | 358/405 |
| 6,031,914 A | * 2/2000 | Tewfik et al. | 380/54 |
| 6,061,793 A | * 5/2000 | Tewfik et al. | 713/176 |
| 6,208,735 B1 | * 3/2001 | Cox et al. | 380/54 |

OTHER PUBLICATIONS

Areepongsa et al. (Steganography for a low bit-rate wavelet based image coder, Jul. 2000, IEEE).*

Areepongsa et al. (Exploring steganography for low bit rate wavelet based coder in image retrieval system, Aug. 2000, IEEE).*

Chae et al. (A robust embedded data from wavelet coefficients, Dec. 1997, SPIE, vol. 3312).*

Inoue et al. (A digital watermark technique based on the wavelet transform and its robustness on image compression and transformation, SCIS, 1998).*

Onishi et al. (Wavelet detection of watermark from a clipped picture using wavelet, Jul. 1997, ITE Technical).*

Ishizuka et al. (On an experimental evaluation of steganography with wavelet transform, SCIS, 1997).*

Matsui et al. (Embedding a signature to pictures under wavelet transformation, Jun. 1996, IEICE).*

Cooklev et al., Two-Channel Multifilter Banks and Multiwavelets, IEEE Publication No. 0-7803-3192, Mar. 1996.

* cited by examiner

Primary Examiner—Andrew W. Johns
Assistant Examiner—Amir Alavi
(74) Attorney, Agent, or Firm—Workman, Nydegger & Seeley

(57) ABSTRACT

The disclosed watermarking method utilizes a transform technique for inserting an imperceptible digital watermark into digital data that is strongly resistant to unauthorized detection and decoding. Methods for embedding a watermark that is sufficiently robust to lossy compression and other image processing operations such as rescaling are also provided. The watermarking principle is based on wavelet transforms where the coefficients of the filters have binary values, and are thus very attractive for practical realization. The wavelet filters utilize complimentary polynomials and implement non-regular wavelet transforms upon which the digital watermark is inserted. Following the inverse transformation process, the digital watermark is spread across multiple frequencies of the original digital data thereby reducing the impact of signal processing operations such as compression or other frequency filtering based operations. Additional embodiments employing complimentary matrix polynomials which are closely related to multifilter banks are also provided.

23 Claims, 6 Drawing Sheets

METHOD AND APPARATUS FOR WAVELET-BASED DIGITAL WATERMARKING

BACKGROUND OF THE INVENTION

1. The Field of the Invention

The present invention generally relates to the field of digital imaging of multimedia data. More particularly, the invention relates to embedding a sufficiently robust watermark into the image data that can withstand lossy compression schemes without degrading the digital watermark.

2. Present State of the Art

The number of applications that use digital storage and transmission is increasing at a rapid rate. Specifically, types of digital data include digital audio, digital images and digital video, which may be largely electronically distributed over ubiquitous public networks such as cable and telephone infrastructures. Additionally, digital data may be physically exchanged and replicated into exact duplicates of the original.

The proliferation of digital media, e.g., audio, image and video, creates property concerns relating to intellectual property rights, e.g., copyrights. Traditional cryptographic techniques have provided one level of protection by allowing decryption of the encrypted data to be performed only by decryption key holders. However, conventional cryptography provides little protection against data piracy, i.e., unauthorized reproduction of decrypted digital data, since decrypted digital data may be easily replicated and distributed. Such schemes provide insufficient protection against unauthorized reproduction of information and the inability to determine the source or origin of unauthorized duplicates.

It is known in the prior art to provide a "digital watermark" on a document to address this problem. Traditional digital watermarks on a data file or document may be perceptible and even visible or may be sufficiently embedded within the digital data so as to be imperceptible to those perceiving the digital data. Such digital watermarks remain present within the data even after processing such as a decryption procedure. While visible or humanly perceivable digital watermarks may provide apparent identification of the incorporating entity, such as a copyright owner, noticeable digital watermarks are considered unacceptable for aesthetically integrous media, e.g., imaging and audio data.

Imperceptible watermarks are comprised of an identification code that is permanently embedded within the digital data and may contain specific information such as the identity of the purchaser of a particular copy of the digital data, e.g., audio (speech and music), images (photographic and graphics) and video (movies).

There are techniques that have been proposed for watermarking digital data. In U.S. Pat. No. 5,464,997 to Barton, a method and apparatus is disclosed for basic authentication of a digital block such as an image carrying authentication information provided by the user embedded into the digital block of data. A digital signature comprised of a reduced representation of the digital block of data is embedded by replacing predetermined bits within the digital block of data. The authentication process is performed in reverse order so as to expose the embedded digital signature, thereby authenticating the integrity of the digital block of data. It should be pointed out that such an implementation while adequate for digital data transmission and storage techniques that do not impose compression techniques, are wholly inoperative in modern communication channels that employ sophisticated modulation techniques and other lossy compression methods. While it is possible to employ techniques such as those that use the least significant bits (LSBs) of the image data to conceal or embed the digital watermark, such approaches are obviously not sufficiently robust for enduring lossy compression processes as lossy compression techniques tend to randomize the LSBs. Furthermore, employing the most significant bits of the data image renders the digital watermark perceptible and therefore unacceptable or undesirable for aesthetically demanding forms of digital data. Additionally, employing a frequency transformation followed by embedding the digital watermark in the high frequency bands is also insufficiently robust since elementary lowpass filtering results in the decimation of the digital watermark. Conversely, placing the digital watermark in the low frequency components causes the digital watermark to become perceptible and therefore aesthetically unacceptable. Therefore, it should be apparent that the objectives of creating an imperceptible digital watermark that is additionally sufficiently robust to lossy image processing, e.g., compression and rescaling, are in direct conflict. That is to say, if the digital watermark is sufficiently robust to lossy imaging processing operations, the digital watermark becomes perceptually significant and therefore unacceptable. Conversely, embedding the digital watermark so as to be imperceptible results in an inadequately robust digital watermark.

It is known that orthogonal transforms e.g., Discreet Cosine Transform (DCT) and Discreet Fourier Transform (DFT), can be used to perform digital watermarking in the transform domain as taught in Cox et al., *Secure Spread Spectrum Watermarking for Images, Audio and Video*, Proceedings of the 1996 International Conference on Image Processing, Vol. III, pp. 243–246, 1996. In that particular public description, the authors propose inserting a watermark into the spectral components of the digital data using techniques analogous to spread spectrum communications, i.e., hiding a narrow band signal in a wide band channel which is represented by the digital data. However, in such DCT-based approaches, spectral energy is concentrated which facilitates data compression, but becomes disastrous for retaining the integrity of the digital watermark.

In such DCT-based approaches, the low-frequency components are employed, but the mean-value coefficient is excluded. Such an implementation suggests that the DCT-based approaches are not systematic. Such approaches were studied and proposed by Cox et al. due to the popularity of DCT in the industry. Therefore, orthogonal transforms such as the DCT or the DFT are good choices for compression, but are less than desirable choices for digital watermarking. The fundamental disadvantage of such techniques result from the fact that such techniques offer energy compaction and are therefore not sufficiently adequate choices for a spread spectrum-based algorithm.

Thus, it appears that there exists no digital watermarking scheme that is capable of embedding an adequately imperceptible digital watermark into a digital data file, wherein the digital watermark is sufficiently robust to withstand lossy image processing operations (e.g., compression and resealing), while remaining detectable following such degradation processing. There also does not exist any digital watermarking technique that is sufficiently strongly resistant to unauthorized detection and decoding, even by individuals cognizant of the present watermarking techniques. Finally, there exists no digital watermarking technique that may be applied to all media types, e.g., audio, images, video, graphics and text (when represented as an image), that may be universally applied.

SUMMARY AND OBJECTS OF THE INVENTION

It is an object of the invention to provide a method for watermarking digital data in such a manner as to cause the digital watermark to remain resilient throughout lossy compression processes.

It is a further object of the present invention to provide a method for designating and determining the origin of digital data which may be subjected to lossy compression techniques through the use of a digital watermark.

It is a further object of the present invention to provide a method for spreading a digital watermark across digital data such that when a portion of the frequencies of the digital data are compressed and thereby disposed, the digital watermark remains intact and discernable.

Yet another object of the present invention is to provide a method for determining the origin of a particular copy of digital data through the use of a digital watermark adequately embedded within the digital data such that lossy compression techniques do not obscure or degenerate the digital watermark.

It is yet another object of the present invention to provide a method for determining the legitimacy of a copy of digital data which has a digital watermark embedded thereon.

It is yet another object of the present invention to provide a digital watermark that is imperceptible when embedded within digital data and is thereby aesthetically acceptable for marking digital data, such as images, that dictate imperceptible steganography or embedding of data such as a digital watermark.

It is a further advantage of the present invention to provide a digital watermarking technique that is strongly resistant to unauthorized detection and decoding even to those familiar with the watermarking technique of the present invention.

Yet another advantage of the present invention permits graceful degradation, such as lossy compression, of the digital data having the watermark embedded thereon while retaining the integrity of the watermark following a decompression process.

It is yet another advantage of the present invention to provide a universal watermark that can be applied to a myriad of media types, (e.g., audio, images, video, graphics and text when represented as an image), while being implemented in a practical and efficient implementation that is conducive to computerized processing.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a method and apparatus for digitally watermarking digital data is presented which is visually imperceptible and strongly resistant to unauthorized detection and decoding. Furthermore, the watermarking technique of the present invention is robust to lossy compression and other image processing operations such as rescaling. The watermarking principle of the present invention is based on wavelet transforms where the coefficients of the filters have binary values, and thus are very attractive for practical realization. These wavelet filters are related to complimentary polynomials, which are also related to multifilter banks. Experimental results have shown that multifilter banks, in addition to scalar filter banks, are advantageous for applications such as that of the present invention.

Those skilled in the art of digital signal processing appreciate that the number of applications that use digital storage and transmission is increasing at a rapid rate. Such applications include digital audio, images and video, transmission of video over public networks (e.g., cable and telephone networks). Therefore, protection of these various forms of digital data are fundamental to securing certain rights, such as intellectual property rights, that enure to the benefit of the right holder. For example, publishers and artisans have long relied upon access control (i.e., physically controlling access) to provide security to their works. Subsequent techniques such as cryptography have provided limited protection against unauthorized reproduction by restricting those individuals that are authorized or retain the decryption algorithm for decrypting their artistic work. However, once the data is decrypted, it is freely copyable without a trace of information describing the origin of the casually protected data. To provide a tag or other identifying information, prior implementations have utilized a digital watermark which was perceptually significant and thereby degraded the aesthetic value of the digital data. Furthermore, attempts to place watermarks throughout digital data have often been destroyed by image processing techniques such as data compression operations. If a watermark is to be robust to lossy image processing operations, it may become perceptually significant unless, as in the present invention, the digital watermark is spread across the digital data.

Those skilled in the art of digital signal processing appreciate the value of transforming spatial data into a transform domain, such as the frequency domain, in which signal processing operations may be performed. One popular transform is the discreet cosine transform (DCT). While a DCT process could be employed for embedding a watermark, the primary disadvantage of the DCT is that it offers energy concentration, as opposed to energy spreading which is necessary for a robust method of embedding a durable watermark. Yet another transform technique appreciated by those of skill in the art is the wavelet transform which, however, also provides energy compaction and even more so than the DCT. Therefore, traditional or regular wavelets, the most prominent of which are the Daubechies wavelets, are less desirable choices for watermarking. Those of skill in the art appreciate that regular wavelets are continuous functions which implies that the impulse responses of the filers which tenerate them are relatively smooth.

While it is not wholly appreciated, there are other types of wavelets, such as non-regular wavelets or wavelets which do not provide continuous functions. Non-regular wavelets have completely contrasting physical properties from regular wavelets. For example, they do not generate multiresolution analysis and although the filter coefficients form orthogonal bases for the Hilbert space in the discrete-time case, non-regular wavelet functions do not form orthogonal bases for the Hilbert space of continuous-time functions. It is known that complimentary polynomials are intimately related to wavelets, and in fact, these complimentary polynomials are highly non-regular wavelets with coefficients having two values, 1 and −1. An additional embodiment of the present invention employs complimentary matrix polynomials which are related to multiwavelets.

The present invention employs a suggested watermarking algorithm wherein the digital data or digital signal is partitioned into blocks, which are not necessarily of the same length, but are partitioned such that the amplitude of the signal within a block does not change or vary significantly. A subsequent step of the watermarking algorithm of the present invention is to generate a subband tree that is either a pruned or a complete subband tree through which the wavelet transform may be performed. While a complete subband tree may be employed, additional security is derived by employing uniquely pruned subband trees. The forward orthogonal circular wavelet transform, or alternatively the multiwavelet transform, may be performed such that the filter coefficients have only two values, 1 and −1. Additionally, the polyphase components of the filters are complimentary sequences.

The next step of the watermarking algorithm is to insert the watermark by modulating some or all of the wavelet coefficients. Since the wavelets are highly non-regular, this is equivalent to placing the watermark everywhere in the frequency domain. The watermark itself may be a sequence of random numbers or it may be a predetermined sequence such as an ASCII text string. Both imperceptible and perceptible watermarks may be employed as long as the aesthetic qualities of the digital data are not significantly impaired. Following the insertion or overlaying of the digital watermark, the inverse orthogonal circular wavelet transform is performed with the corresponding synthesis filter bank to obtain the watermarked digital data. The watermarked digital data may be compressed, transmitted, filtered or otherwise processed with the watermark remaining discernable and intact.

The algorithm for verifying whether unknown digital data incorporates a specific watermark may be performed by decomposing the digital data into blocks as was performed during the embedding process. Subsequently, the same subband tree as was utilized in the embedding processing, either a complete or pruned subband tree is reconstructed for the wavelet transform. A forward wavelet transform is performed on the unknown or distributed watermarked data to determine the wavelet coefficients. Likewise, a forward wavelet transform is performed on a previously stored copy of the original digital data, also known as the reference data, to determine the wavelet coefficients of the pristine or reference digital data. The wavelet coefficients of both of the forward transformed digital data (unknown data and reference data) are compared to extract a difference which would be representative of any watermark data present within the unknown digital data. The extracted or corrupted difference sequence representing any resident watermark is compared with the watermark or reference watermark stored previously during the embedding process. If the extracted watermark sequence is sufficiently close, (i.e. within a predefined verification threshold), such as if the extracted watermark sequence coincides with more than fifty percent of the reference watermark, then it is concluded that the watermark is present in the unknown data. If the watermark is a random sequence, compared with the reference watermark, then it is determined that either the digital watermark was not present in the unknown data or the unknown data was sufficiently corrupted to make the verification process statistically challenging.

The watermarking technique of the present invention is robust to unauthorized detection, even if an attacker knows the original image and watermarking principle, (i.e., even if the attacker knows that a wavelet transform has been used and the filter coefficients obtained form a complimentary sequences). To achieve success by an attacker, the attacker must find the exact number of filter coefficients and the exact values of these coefficients. Since the number of different complimentary polynomials grows exponentially with their length, such an attack cannot be accomplished in a reasonable amount of time. Secondly, the attacker must also find the exact subband tree that has been employed. Any randomly pruned subband tree can be used in the watermarking process of the present invention. Thirdly, since there are even more complimentary matrix polynomials than scalar complimentary polynomials, one may use multiwavelet transforms to achieve an even higher level of security.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

These and other objects and features of the present invention will become more fully apparent from the following description and appended claims or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The current invention embraces within its scope a method and apparatus for digitally watermarking digital data. Thus, the descriptions of the preferred embodiments which follow should be read to include both methods and apparatuses. With particular regard to the apparatuses involved, no particular limitation is envisioned. Thus, the apparatus may involve dedicated hardware including discreet components, shift registers, custom VLSI chips, and the like, as well as general purpose computer or digital signal processing hardware having a conventional arrangement including a processing unit, memory, input devices, display devices, mass storage devices, and the like. From the description which follows, those skilled in the art will recognize that a variety of hardware and/or software configurations are suitable apparatuses for practicing the disclosed invention.

Figure 1:
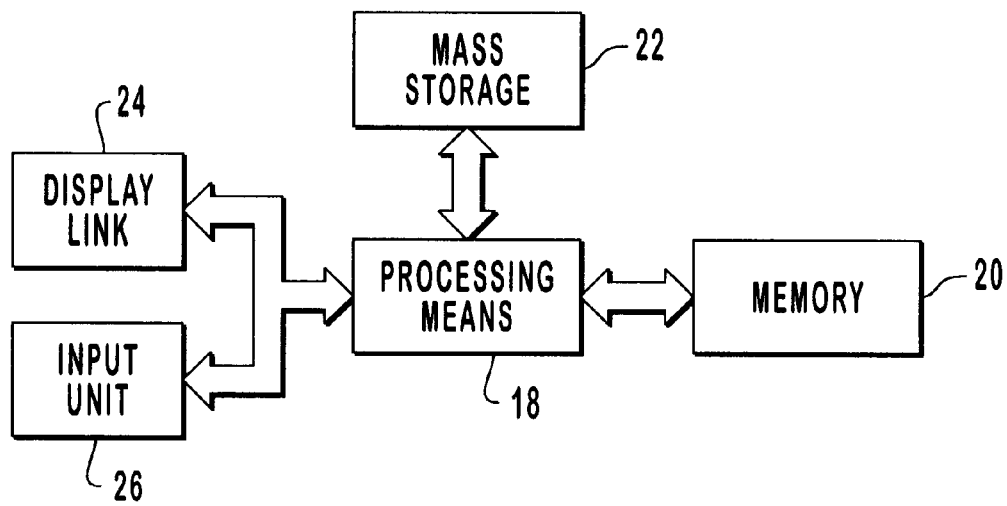
FIG. 1 is a high level block diagram showing an example apparatus structure, employable by the embodiments of the present invention.

By way of example, and not limitation, a suitable hardware apparatus is illustrated in FIG. 1. In FIG. 1, the apparatus comprises processing means 18. Processing means 18 preferably comprises a general purpose microprocessor like those commonly used in personal computers or workstation computers. Processing means 18 could, however, also comprise a digital signal processor, a specialized processor custom tailored to the inventive method disclosed herein, or any combination of a general purpose microprocessor, a digital signal processor, and a specialized processor.

Electrically connected to processing means 18 is memory 20. Memory 20 is preferably comprised of a combination of both volatile and non-volatile memory. Depending on the application, however, memory 20 may also comprise either solely volatile or solely non-volatile memory.

Processing means 18 is also electrically connected to mass storage 22. Mass storage 22 preferably comprises a combination of fixed and removable computer disk storage (either magnetic or optical) although the apparatus could be configured with only fixed computer disk storage or removable disk storage.

Computer usable medium having computer-readable code means embedded or encoded thereon is also contemplated. In such an article of manufacture, the computer readable program code means will comprise various means for implementing the method disclosed herein. By way of example, and not limitation, suitable computer usable media include magnetic disks (both fixed and removable), optical, magnetic tape, volatile memory, non-volatile memory, and the like. In these articles of manufacture, the term "embedded therein" should be read to include the various methods of encoding computer-readable program code means so they are contained on or in the computer usable media.

Throughout this application, the invention is described in relation to digital data. By way of example, and not limitation, digital data include image data both fixed and video, audio data, as well as other forms of digital data including textual data represented as an image.

Figure 2:
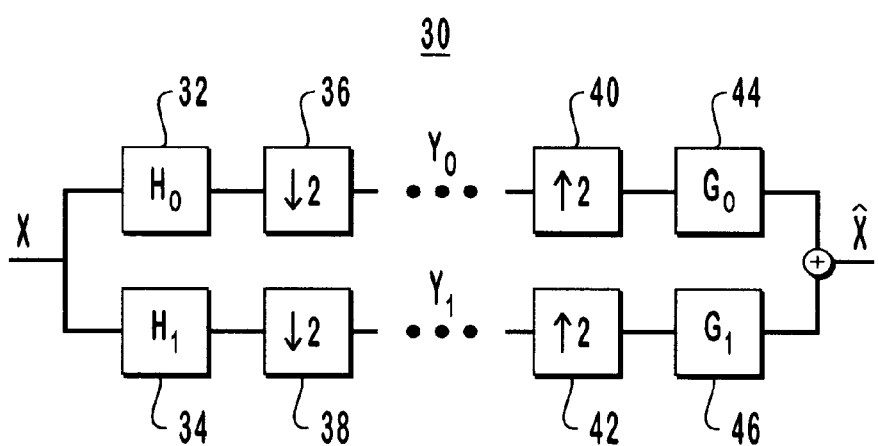
FIG. 2 is a depiction of a two channel orthogonal FIR filter bank, in accordance with a preferred embodiment of the present invention.

The present invention employs digital signal processing techniques for manipulating and processing the digital data of the present invention. The mathematical implementation of the processing techniques are first introduced followed by the specific methods employed by the present invention. For digital signal processing applications, two channel orthogonal finite impulse response (FIR) filter banks are among the most widely used class of filter banks. FIG. 2 depicts a typical two channel orthogonal FIR filter bank 30 which is typically comprised of two parts. In a first part, an analysis part is comprised of two filters, $H_0(z)$ 32 and $H_1(z)$ 34, which are each followed by downsamplers 36 and 38, respectively. Filter bank 30 is further comprised of a synthesis or reconstruction portion comprising upsamplers 40 and 42 followed by two filters, $G_0(z)$ 44 and $G_1(z)$ 46.

The two signals exiting the analysis part, may be denoted by $Y_0(z)$ and $Y_1(z)$ and called subband signals, and are equal to:

$$Y_0(z)=\tfrac{1}{2}[H_0(z^{1/2})X(z^{1/2})+H_0(-z^{1/2})X(-z^{1/2})]. \qquad (1)$$

$$Y_1(z)=\tfrac{1}{2}[H_1(z^{1/2})X(z^{1/2})+H_1(-z^{1/2})X(-z^{1/2})]. \qquad (2)$$

It is shown that the output signal, $\hat{X}(z)$ is given by $$\hat{X}(z)=\tfrac{1}{2}[H_0(z)G_0(z)+H_1(z)G_1(z)]X(z)+ \qquad (3)$$

$$\tfrac{1}{2}[H_0(-z)G_0(z)+H_1(-z)G_1(z)]X(-z) \qquad (4)$$

In perfect-reconstruction (PR) filter banks, $\hat{X}(z)=X(z)$ and therefore $$H_0(z)G_0(z)+H_1(z)G_1(z)=2. \qquad (5)$$

$$H_0(-z)G_0(z)+H_1(-z)G_1(z)=0. \qquad (6)$$

The transform which represents the computation of the two subband signals $y_0[n]$ and $y_1[n]$ from $x[n]$ is called a forward wavelet transform. The transform which computes the signal $\hat{x}[n]$ (which is equal to $x[n]$ provided the filter bank is PR) is called an inverse wavelet transform. Note that PR is very important even though the signals $y_0[n]$ and $y_1[n]$ are often perturbed in a controlled fashion prior to reconstruction. The sole reason for the deviation from PR lies in the additional processing of the subband signals.

In orthogonal filter banks, the impulse response $h_0[n]$, together with its integer, translates to form an orthogonal basis for the Hilbert space of square summable sequences. The aperiodic auto-correlation function (ACF) of the impulse responses, $h_0[n]$ and $h_1[n]$, are half-band functions:

$$<h_0[n], h_0[n+2k]>=\delta_k, \qquad (7)$$

$$<h_1[n], h_1[n+2k]>=\delta_k, \qquad (8)$$

while the cross-correlation is identically zero $$<h_0[n], h_1[n+2k]>=0 \qquad (9)$$

Any two sequences $h_0[n]$ and $h_1\{n\}$ that satisfy (7), (8) and (9) form an orthogonal two-channel FIR filter bank and the two sequences can be used for signal expansion of square-summable sequences. The synthesis filters are completely determined from the analysis filters:

$$G_0(z)=H_1(-z)=z^{-N}\tilde{H}_0(z) \qquad (10)$$

$$G_0(z)=H_1(-z)=z^{-N}\tilde{H}_1(z), \qquad (11)$$

where the . operation means transposition conjugation of the coefficients and replacing z by $z^{-1}$. The highpass filter is related to the lowpass as $$H_1(z)=z^{-N}\tilde{H}_0(-z), \qquad (12)$$

where N is the order of the filters and is necessarily odd. The product filter $P(z)$ is very important $$P(z)=H_0(z)G_0(z)=H_0(z)H_1(-z)=H_0(z)\tilde{H}_0(z)z^{-N} \qquad (13)$$

A necessary and sufficient condition for perfect-reconstruction is that $P(z)$ is half-band:

$$P(z)+P(-z)=2z^l. \qquad (14)$$

Splitting the even-indexed and odd-indexed coefficients is called a polyphase decomposition:

$$H_0(z)=H_{00}(z^2)+z^{-1}H_{01}(z^2), \quad (15)$$

$$H_1(z)=H_{10}(z^2)+z^{-1}H_{11}(z^2). \quad (16)$$

From (12) the relationship between the polyphase components of the two filters can also be obtained.

$$H_{10}(z)=z^{-(N-1)/2}\tilde{H}_{01}(z), \quad (17)$$

$$H_{11}(z)=-z^{-(N-1)/2}\tilde{H}_{00}(z). \quad (18)$$

While those skilled in the art appreciate that digital filter banks were originally developed in the 1970's and 1980's, with the main application of filter banks in the area of data compression. Subband coding of audio, images and video, as the method is typically called, provides one of the competing technologies for data compression and provides several theoretical and practical advantages including multiresolution analysis, interoperability and fast and efficient computation. Those skilled in the art also appreciate that I. Daubechies discovered that orthogonal filter banks provide orthogonal bases for the Hilbert space of square-summable sequences and further demonstrated that when the filters satisfy constraints in addition to perfect-reconstruction, regular or smooth continuous-time functions, (e.g. scaling functions and wavelets,) may be obtained which are orthogonal bases for the space of square-integrable functions. It should be pointed out that filter banks have been designed such that in addition to perfect reconstruction, the filters have acceptable and even good frequency responses, i.e., $H_0(z)$ has always been required to be a reasonably good lowpass filter and $H_1(z)$ has also been required to be a reasonably good highpass filter. Such a requirement of the filter banks provides energy concentration leading to exceptionally good compression capabilities. However, wavelets, which do well for image compression, also offer energy compaction even more so than orthogonal transforms. Therefore, those skilled in the art appreciate that Daubechies wavelets, the most prominent orthogonal regular wavelets, do not have the spread spectrum capability, since they are intended for image compression. However, up until this point, the only type of wavelets that were generally known were what will be called "regular wavelets" in which energy compaction resulted. However, wavelet transforms that offer energy spreading, such as "non-regular wavelets" provide energy spreading and thus are very suitable for digital watermarking. In the present invention, filter banks where the filters $H_0(z)$ and $H_1(z)$ are not "good" filters in the traditional sense, (i.e., the corresponding filters of the present invention display a pseudo-noise frequency response are employed).

The present invention employs the theory of Golay-Rudin-Shapiro sequences, also known as complimentary sequences, which by definition consist of two finite sequences $$A=(a_0, a_1, \ldots, a_l), \quad (19)$$

$$B=(b_0, b_1, \ldots, b_l), \quad (20)$$

of 1's and −1's such that the sum of autocorrelation functions of the two sequences is constant:

$$A(z)A(z^{-1})+B(z)B(z^{-1})=2l, \quad (21)$$

where the polynomial notation has been used:

$$A(z) = \sum_{i=0}^{l-1} a_i z^{-i}$$

and $$B(z) = \sum_{i=0}^{l-1} b_i z^{-i}.$$

Polynomials of order N may be constructed with coefficients equal to 1 or −1, such that $|P(z)|$ is minimal as z ranges over the unit circle. Those skilled in the art appreciate that the coefficients to the pairs of polynomials are known as the Rudin-Shapiro polynomials or equivalently the Golay sequences or, alternatively under a combined name known as the Golay-Rudin-Shapiro (GRS) sequences.

Those skilled in the art appreciate that a Golay pair is known as a kernel if it cannot be obtained by a transform method from Golay pairs of the same length, nor derived from Golay pairs of shorter lengths. Kernels of lengths 2, 10 and 26 have been found by computer research and methods exists, known by those of skill in the art, for employing these kernels to construct Golay pairs of lengths $2^a 10^b 26^c$. It is presently unknown whether other kernels exist. Those skilled in the art should appreciate that while there are perfect-reconstruction FIR filter banks of every even length, the requirement that the length of the Golay sequences be even is not sufficient. Furthermore, the question of the possible lengths of the Golay sequences is an open yet unsolved difficult problem. In addition to the requirement that l be even, l must be the sum of two integral squares and must satisfy other conditions appreciated by Golay in his earlier research. Prior to the development of wavelet transforms, it was appreciated and recognized that Golay pairs provided orthonormal bases for the Hilbert space. Additionally, complementary sequences have found various applications in wireless communication systems (e.g., CDMA) and other data communication systems.

It has recently been shown that the GRS sequences are a special case of orthogonal FIR filter banks. That is to say, the GRS polynomial pairs are polyphase components of a lowpass filter in an orthogonal maximally-decimated two-channel FIR filter bank. Such a statement may be proved by supposing that given a filter $H(z)$ of length $2l-1$ with coefficients which are either +1 or −1, it must satisfy $$H(z)H(z^{-1})+H(-z)H(-z^{-1})=\text{const}=4l. \quad (22)$$

It can be proved that the polyphase components of $H(z)$ satisfy (21), i.e. they form a GRS polynomial pair:

$$4l=[H_0(z^2)+z^{-1}H_1(z^2)][H_0(z-2)+zH_1(z^{-2})]$$

$$+[H_0(z^2)+z^{-1}H_1(z^2)][H_0(z-2)+zH_1(z^{-2})]$$

$$=2[H_0(z^2)H_0(z^{-2})+H_1(z^2)H_1(z^{-2})]. \quad (23)$$

Therefore, it is possible to establish that the filter with polyphase components equal to a GRS sequence pair is power-complimentary.

Figure 3:
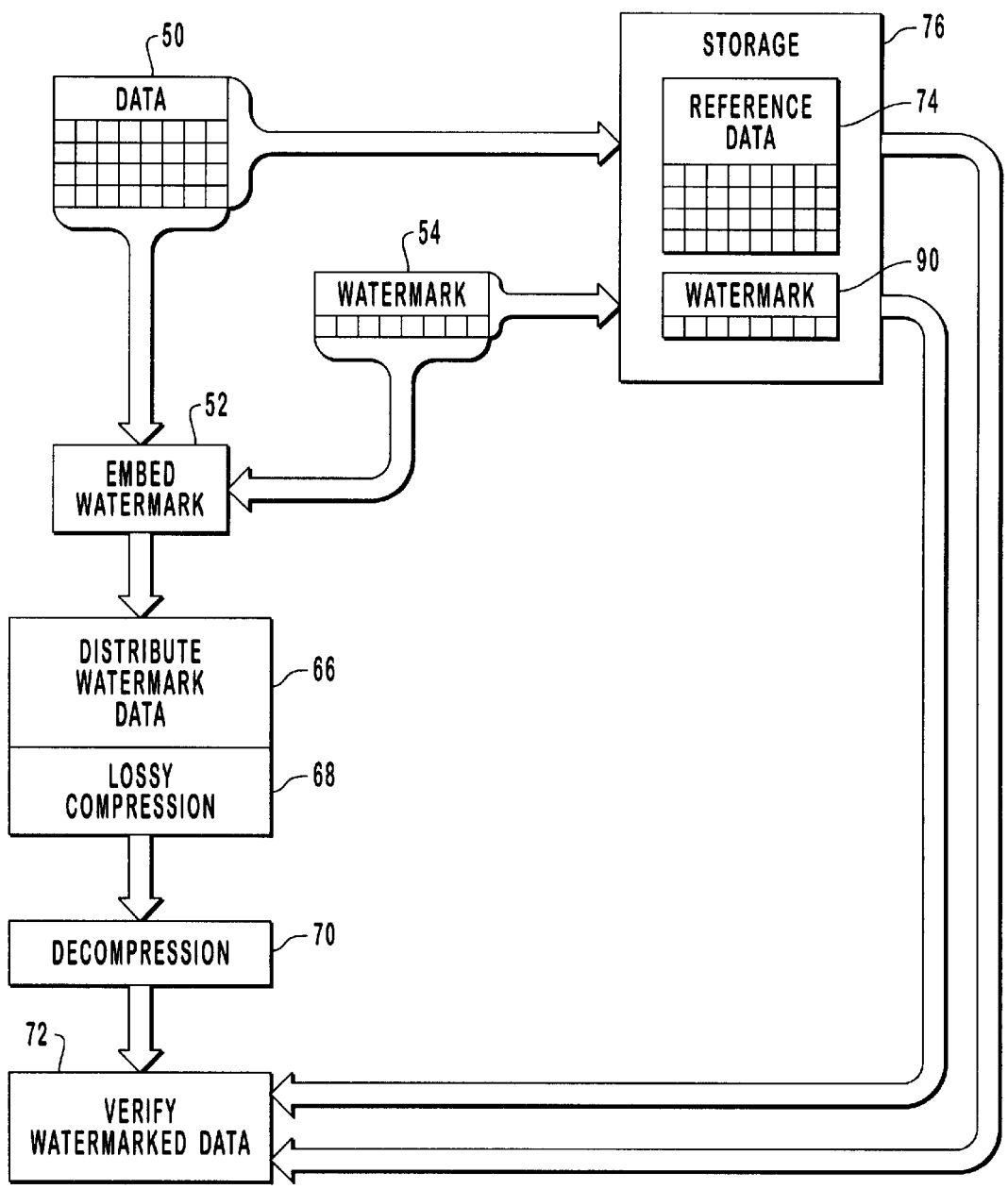
FIG. 3 is a high level block diagram of an embodiment for designating and determining the origin of digital data through the use of a digital watermark, in accordance with the embodiments of the present invention.

FIG. 3 depicts a general overview of the watermarking process of the present invention. Digital data 50 is presented to the present invention to undergo the watermarking process prior to distribution. As previously described, data 50 may take the form of digital data capable of sustaining lossy compression, such as audio, video, image and textual data represented as image data.

Figure 4:
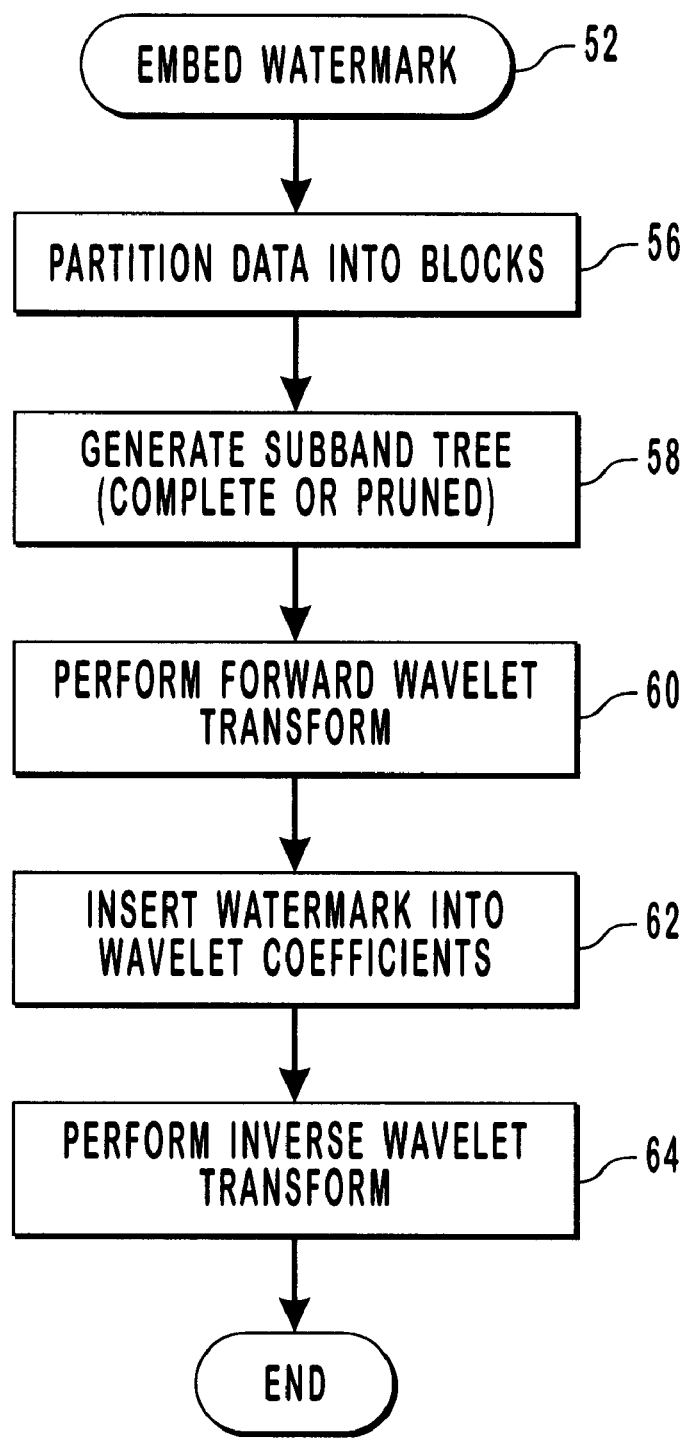
FIG. 4 is a flow chart of the embedding process for embedding a digital watermark in digital data, in accordance with the embodiments of the present invention.

Digital data 50 is presented to an embed watermark process 52 wherein a watermark 54 is embedded into data 50 in such a manner that the watermark remains robust to lossy image processing operations. The embed watermark process 52 is further detailed in FIG. 4. In FIG. 4, a step 56 partitions the digital data or signal into blocks which are not necessarily required to be of the same length. The partitioning of the blocks is performed preferably such that the amplitude of the signal or data within the block does not dramatically vary. Step 56 may alternatively be omitted, but is useful for signals such as speech and audio.

In a step 58, a subband tree is generated for the processing of data 50 in the wavelet domain. Those skilled in the art of wavelet processing appreciate the use of a subband tree which is comprised of bifurcating the original signal into a lowpass filter structure and a separate highpass filter structure. Each of the highpass and lowpass filters are followed by downsamplers as described in FIG. 2. The present invention may operate on an entire or complete subband tree or, alternatively, may function equally as well using a pruned or partial subband tree. Additional security against an authorized attack may be accomplished by employing a randomly pruned subband tree whose random selection is repeatable during a verification process. The coefficient for the filters are obtainable from the preceding equations, as comprehended by those of skill in the art.

The next step of embedding watermark process 52 is a step 60 which performs the forward wavelet transform on data 50. The present invention employs a forward orthogonal circular wavelet or multiwavelet transform where the filter coefficients consists of either a value of 1 or a value of −1. The polyphase components of the filters are complimentary sequences, as described above. The forward wavelet transform of the present invention employs an orthogonal FIR two-channel filter bank having filter coefficient values of either 1 or −1, while the polyphase components of the filters are complimentary sequences. It should be pointed out that while the filter bank theory has been developed assuming linear convolution, in practice circular convolution is used to avoid the increase in the number of samples. The corresponding wavelet transforms are called circular wavelet transforms.

Referring back to FIG. 3, a watermark 54 is passed into embed watermark process 52. In FIG. 4, a step 62 inserts watermark 54 into the wavelet coefficients. The insertion process is implemented, in the preferred embodiment, by modulating all wavelet coefficients using bidirectional or unidirectional coding according to the predetermined binary sequence of watermark 54. In bidirectional coding, the coefficient is incremented to encode a "1" and decremented to encode "0". In the unidirectional coding, the coefficient is left unchanged to encode a "0". In the preferred embodiment of the present invention, a bidirectional coding scheme is employed which, assuming that there are equal numbers of 1's and 0's in the watermarking sequence, preserves the mean value of data 50. Those skilled in the art of signal processing appreciate that the present invention employs wavelets that are highly non-regular which results in the placing of watermark 54 spatially across the frequency domain. Furthermore, watermark 54 may be implemented as a sequence of random numbers or may be implemented as a pre-determined sequence, such as an ASCII text string, or a combination such as an ASCII name of a business entity followed by a sequential identifier such as a particular serial number or user identification number.

In a step 64, the wavelet based watermarking algorithm of the present invention computes the inverse wavelet transform using the corresponding synthesis filter bank described above in equations corresponding to $G_0(z)$ and $G_1(z)$ as depicted in FIG. 2. As with the forward transform, the inverse transform of step 64 also employs an orthogonal circular wavelet transform. While the steps of generating a subband tree and performing forward and inverse wavelet transforms may be appreciated by those skilled in the art, the present invention employs specific non-compressive transforms that perform in nontraditional ways by providing non-regular responses for spreading the energy associated with data 50. Additionally, the present invention further obtains its success not only from the choice of the transform, but also from the specific filters that are employed.

In FIG. 3, the watermarked data may be distributed in a step 66 through a communication channel or other channels to end users. While watermarked data may be directly distributed to end users or data consumers, finite limitations and practicalities of communication channel and storage medias frequently dictate that the data undergo compression or data reduction processes. FIG. 3 depicts one such compression process in lossy compression process 68. The term "lossy compression" describes compression techniques wherein data is reduced or encoded in such a manner as to make the reverse process incapable of reconstructing the original data in its entirety. Watermarked data that undergoes lossy compression process 68 and is thereafter subjected to pre-processing process 70 results in watermarked data that differs from the original watermarked data generated as a result of embedding the watermark in process 52. The nature of the watermarking process of the present invention is sufficiently robust to permit the watermarked digital data signal to be compressed, transmitted and even filtered.

There are many applications envisioned in which the watermarking process provides substantial benefits. There are a number of technologies developed wherein protection from illegal copying is deemed critical and even essential. While techniques such as encryption have been employed, encryption protects content during the transmission of the data from the sender to the receiver. However, upon receipt and decryption, the data in its unencrypted form is no longer protected from subsequent copying. Watermarks, however, compliment encryption by embedding a signal or watermark directly into the data. Such an application may provide control for applications such as copyright protection which may include the embedding of a serial number or other indicator within the data. Such embedded data facilitates the determination of the origin of the digital data.

Figure 5:
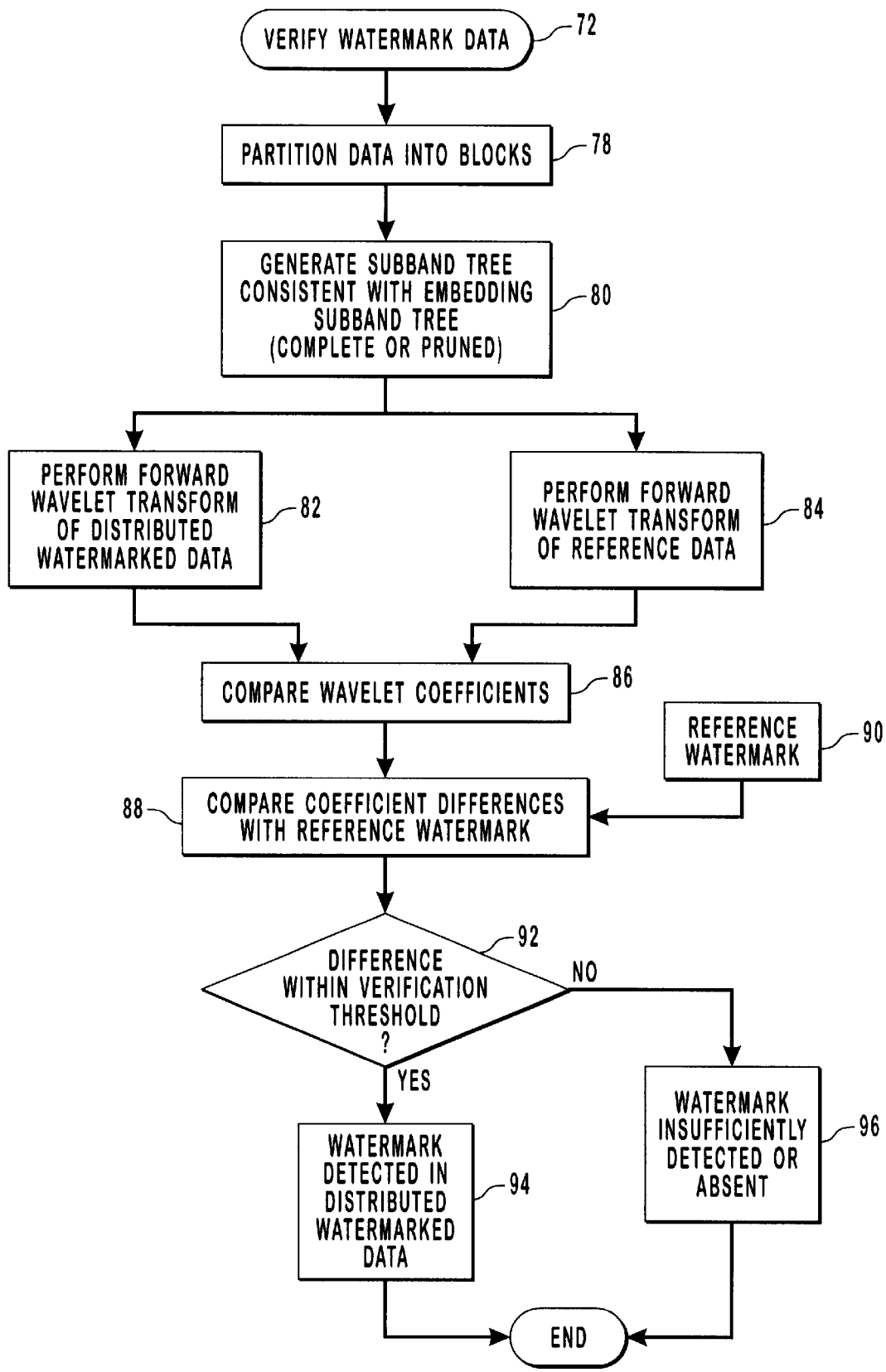
FIG. 5 is a flow chart for verifying the presence of a digital watermark in unknown digital data, in accordance with the embodiments of the present invention.

In order to perform verification process 72 as illustrated in FIG. 3, the present invention employs the storage of data 50 as reference data 74 in a storage device 76. Reference data 74 may be an exact copy of data 50 or may be an exact copy of a portion of data 50 when data 50 is comprised of a significant amount of data, such as in the case where data 50 is video data. Verify watermarked data process 72 is detailed in FIG. 5. Verify watermark data process 72 commences with a complimentary process of the embedding process by partitioning data into blocks in a step 78. Such a decomposition of the signal into blocks, not necessarily of the same length, may be performed such that the amplitude of the signal within a block does not change significantly. In a step 80, the verification process generates a subband tree consistent with the embedding subband tree of the embedding watermark process 52. The subband tree may be implemented as a complete tree or a pruned tree, however, the subband tree must be consistent with the embedding subband tree as subband trees having varying stages or pruned stages which result in erroneous verification transforms when inconsistent with the embedding process subband trees. When a pruned subband tree is employed, an algorithm or description of the pruned subband tree may also be stored in storage 76 (FIG. 3) with reference data 74 and watermark 90.

A step 82 performs a forward wavelet transform of the distributed or unknown watermarked data using the same pair of analysis filters $H_0(z)$ and $H_1(z)$ that were used in the watermarking or embedding process of the distributed watermarked data. Watermarked data wavelet coefficients emerge from the transform process of step 82.

In order to determine whether the watermark is present in the unknown distributed data, a copy or a portion of data 50 stored as reference data 74 (FIG. 3) is utilized by step 84 (FIG. 5) wherein a forward wavelet transform of the reference data is performed. Like step 82, step 84 employs the same subband tree as generated in step 80 which corresponds to the subband tree employed during the embedding process. The transform process of step 84 results in reference data wavelet coefficients.

Step 86 compares the unknown or distributed watermarked wavelet coefficients generated in step 82 with the reference data wavelet coefficients from step 84. Compare coefficients differences step 86 compares the wavelet coefficients of the forward transform of the distributed watermarked data of step 82 with the wavelet coefficients resulting from the forward transform of reference data in step 84. In the comparison step of comparing the wavelet coefficients of the reference data with the watermarked data, an attempt is made to extract the watermarking sequence or difference in the coefficients.

A step 88 retrieves a reference watermark 90 (FIG. 3) stored within storage 76 earlier in the embedding process. The difference in the coefficients are compared against reference watermark 90 with statistical evaluation performed in a query task 92. If the differences between the extracted watermark and the reference watermark are within a defined verification threshold, then a step 94 denotes the detection of the watermark in the distributed watermarked data.

When the difference in the coefficients do not acceptably compare with the reference watermark in query step 92, then a step 96 denotes that the watermark is insufficiently detected or absent in the unknown or distributed watermarked data. In the preferred embodiment, since lossy compression results in the decimation of certain bits, a portion of which may be watermarked data, if more than 50% of the bits in the difference between both the coefficients of the transform distributed watermarked data and the transformed reference data as compared with the reference watermark sequence are identified, then the conclusion is that the watermark is present in the unknown or distributed watermarked data.

The embed watermarking and verification processes of the present invention are additionally robust to unauthorized detection, even if the supposed attacker knows of both the original data and the watermarking principle of the present invention, i.e., even if the attacker knows that a wavelet transform has been used and that the filter coefficients are obtained from GRS sequences. In such a scenario, to achieve success the attacker must find the exact number of filter coefficients and the exact values of these coefficients. That is to say, it can be shown that the total number of different orthogonal filter banks with binary coefficients of lengths N=4, 16, 20 is equal to 32, 192, and 128, respectively. If larger lengths of filter bank coefficients are used, the number of possible orthogonal filter banks increases and performing wavelet decompositions with all such possible combination becomes unrealistic. Additionally, the attacker must find the exact subband tree that has been employed. That is to say, any randomly pruned subband tree can be used in the watermarking process. Therefore, it is clear that the wavelet-based scheme of the present invention offers more flexibility and is more robust to an attack by unauthorized users, compared to the DCT-based approaches of the prior art.

Yet another advantage of the present invention over previous watermarking techniques is the number of bits or the length of a particular watermark, i.e., the number of bits that can be hidden in the data. In the present invention, the coefficients resulting from the wavelet transform are modulated by the watermark, thus, the size of the watermark is equal to the number of pixels in the data or image. In contrast, in a DCT transform, domain modulation of all transform-domain coefficients is not allowed since the watermark either will become visible or will loose the robustness for a modest loss in the quality of the data or signal. Therefore, it is clear that the number of bits that can be encoded in the wavelet-based approach of the present invention considerably exceeds the number of bits that can be encoded using a DCT approach.

Figure 6:
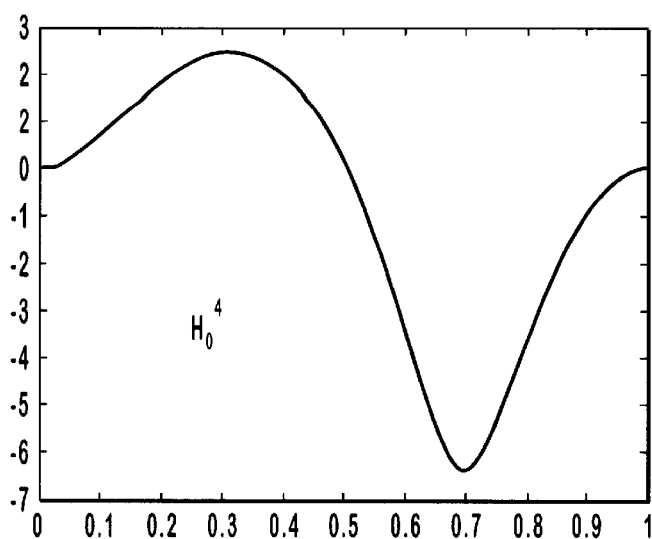
FIGS. 6–8 depict the frequency responses of three exemplary filters depicting the non-regularity of the wavelet transform, in accordance with the embodiments of the present invention.
Figure 7:
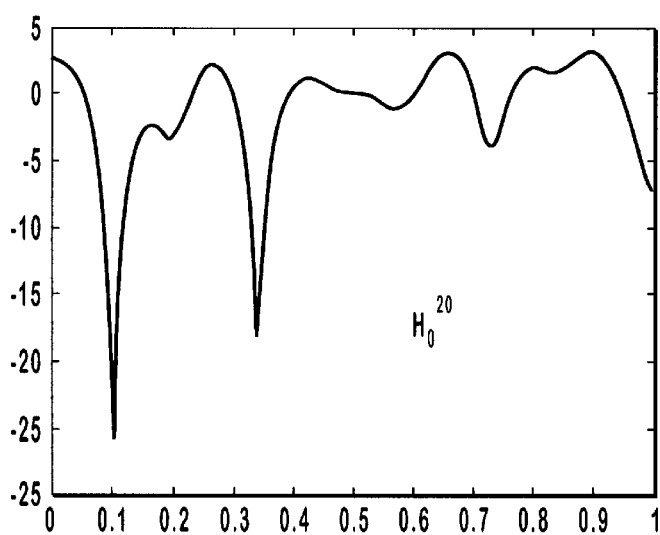
Figure 8:
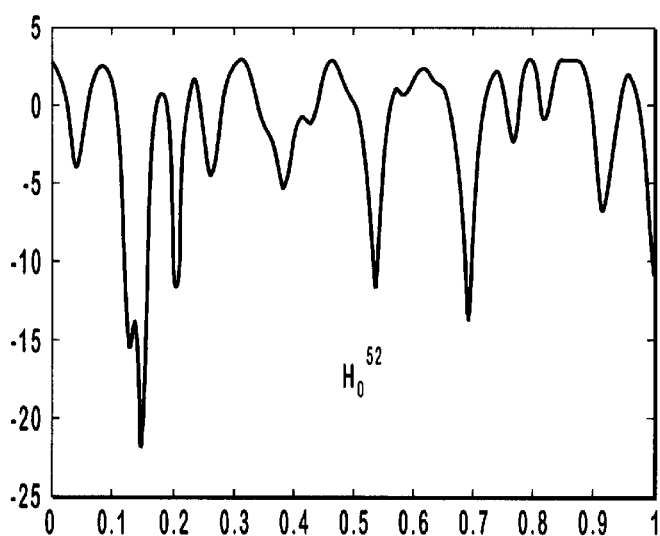

FIGS. 6, 7 and 8 depict experimental results for filters with 4, 20 and 52 coefficients, respectively. The coefficients employed were as follows:

$H_0^4$=(1.0, 1.0, 1.0, −1.0)

$H_0^{20}$=(1.0, 1.0, 1.0, 1.0, −1.0, −1.0, 1.0, 1.0, −1.0, 1.0, 1.0, 1.0, −1.0, 1.0, −1.0, 1.0, 1.0, −1.0, 1.0, −1.0)

$H_0^{52}$=(1.0, 1.0, 1.0, 1.0, 1.0, 1.0, 1.0, 1.0, −1.0, −1.0, 1.0, 1.0, 1.0, 1.0, −1.0, −1.0, −1.0, −1.0, 1.0, 1.0, −1.0, 1.0, 1.0, 1.0, −1.0, 1.0, 1.0, 1.0, −1.0, 1.0, −1.0, 1.0, 1.0, −1.0, −1.0, 1.0, 1.0, −1.0, 1.0, 1.0, −1.0, 1.0, −1.0, 1.0, −1.0, −1.0, 1.0, −1.0, 1.0, 1.0, −1.0, 1.0, −1.0, 1.0, −1.0) (24)

The corresponding filters of $H_1(z)$ which form a PR filter pair are not listed here but can be determined from the above equation (12). In the present invention, these filters have been chosen because they are considered to have short, medium and long impulse responses. It should be reiterated that the restriction that the coefficients be binary, that is to say either a 1 or −1, places severe constraints on the filters. Such filters achieve PR, but do not satisfy the additional constraints of multiresolution analysis and smooth scaling functions of wavelets. Therefore, these filter banks are highly non-regular. Due to their non-regularity, these filters are inoperative for use in compression or data reduction techniques, however, for watermarking there behavior is very acceptable. The frequency responses of the three filters described in equation (24) are depicted in FIGS. 6–8, respectively.

Figure 9:
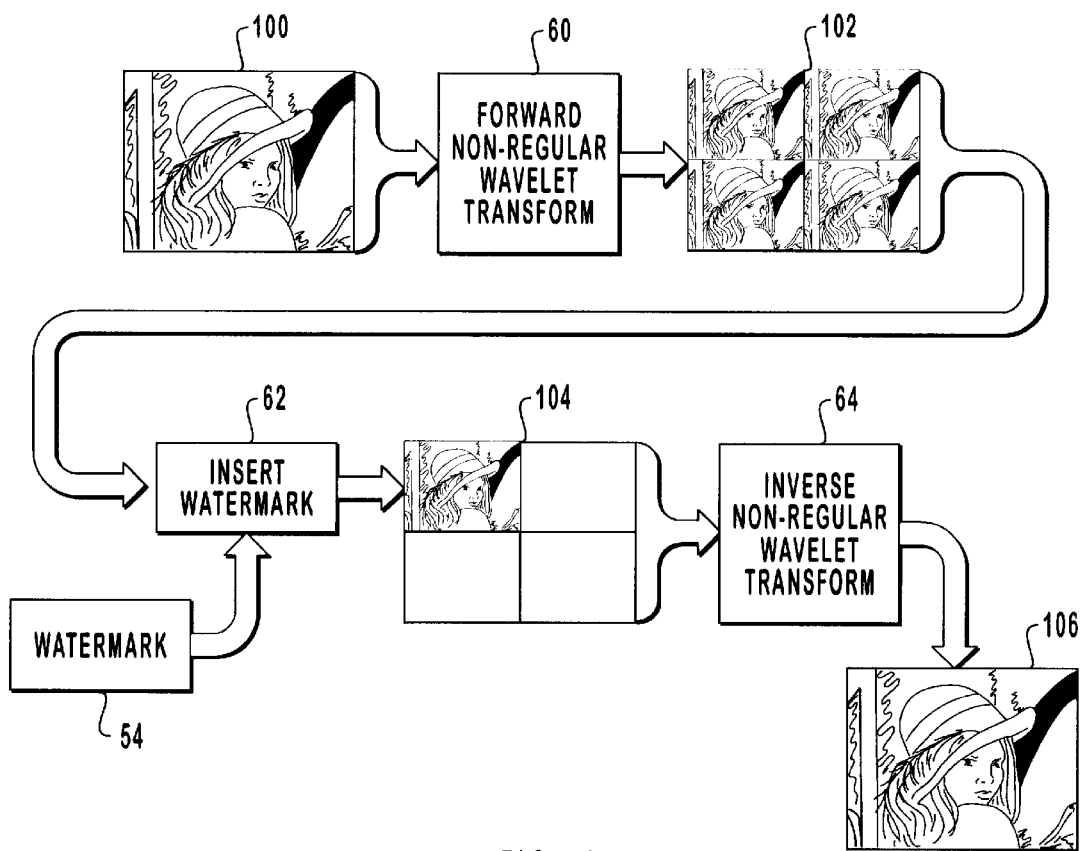
FIG. 9 depicts a simplified flow diagram of digital data undergoing an embedding process for inserting a digital watermark on digital data, in accordance with the embodiments of the present invention.

A simplified graphical depiction is presented in FIG. 9 corresponding to actual test results performed using the present invention. In FIG. 9, image 100 is subjected to the forward non-regular wavelet transform 60 (FIG. 4) for converting image 100 into the wavelet domain. Watermark 54 is thereafter inserted through process 62 into wavelet domain image 102. Watermark 54, as described above, may take the form of an ASCII text string, and in the preferred embodiment is inserted or modulated into the coefficients on each row of the transformed image. Watermark 54 may optionally be repeated on every column, to the maximum extent possible such that every wavelet coefficient is modulated. It should be pointed out that only one iteration of the wavelet transform is used. Therefore, watermark 54 is modulated at both high and low frequencies which causes the watermark to be robust during lossy image processing operations. Following the modulation of watermark 54 onto wavelet transform image 102, the inverse non-regular wavelet transform process 64 (FIG. 4) is performed resulting in watermarked image 106.

In one experiment employing the present invention, the widely used image of "Lena" was processed. In evaluating the effectiveness of the present invention, the watermarked image was subjected to JPEG compression to evaluate the influence of the length of the impulse response.

TABLE 1

Percentage of correctly identified watermarking bits for a 64 × 64 image, compressed by JPEG, and a filter bank with 52 coefficients.

| JPEG Compression Factor | % Correct Bits |
|---|---|
| 7.7 | 73.4 |
| 9.46 | 64 |
| 10.53 | 53 |

TABLE 2

Percentage of correctly identified watermarking bits for a 64 × 64 image, compressed by JPEG, and a filter bank with 20 coefficients.

| JPEG Compression Factor | % Correct Bits |
|---|---|
| 7.7 | 73.4 |
| 9.46 | 56.2 |
| 10.53 | 51.5 |

TABLE 3

Percentage of correctly identified watermarking bits for a 64 × 64 image, compressed by JPEG, and a filter bank with 4 coefficients.

| JPEG Compression Factor | % Correct Bits |
|---|---|
| 7.64 | 90.6 |
| 9.43 | 73.4 |
| 10.90 | 56.2 |
| 11.49 | 57 |
| 12.31 | 59 |
| 13.91 | 51 |

An evaluation of the experimental results and the influence of the length of the impulse response is depicted in Tables 1–3. Tables 1–3 demonstrate the robust nature of the watermarking method of the present invention to JPEG compression, which is a widely accepted image compression standard. It should be pointed out that longer filters or filters with a greater number of coefficients do not achieve better performance, in fact, results demonstrated that shorter filters achieved better performance. Those skilled in the art of image processing appreciate that the JPEG compression algorithm provides perceptually lossless compression for modest values of the compression ratio, however, these values depend on the size of the image as well as the content of the image. From the resultant number of correct watermark bits following image compression, it is apparent that the watermark algorithm is robust to image compression, and only when the image becomes significantly distorted from excessive image compression, does the watermark become irretrievable.

TABLE 4

Percentage of correctly identified watermarking bits for a 64 × 64 image and a filter bank with 4 coefficients. The image is being subjected to decimation and interpolation.

| Compression Factor | % Correct Bits |
|---|---|
| 10.24 | 54.6 |
| 18.20 | 59.3 |
| 40.96 | 57.8 |
| 113.78 | 54 |
| 163 | 54 |

TABLE 5

Percentage of correctly identified watermarking bits for a 32 × 32 image ("Lena"), compressed by JPEG and a filter bank with 4 coefficients.

| JPEG Compression Factor | % Correct Bits |
|---|---|
| 30.50 | 82.2 |
| 33.47 | 80.2 |
| 54.04 | 58.5 |
| 74.31 | 52.3 |

Table 4 depicts the resiliency of the watermark method of the present invention to image resizing which is a very common image processing procedure. In the present example, the input image is filter by a lowpass filtered and downsampled. To identify the watermark, the downsampled image is interpolated to the original image size that was used when the watermark was embedded. Through such a process, even when a 64×64 image is decimated to a 5×5 image, the watcrmarking algorithm of the present invention still retains a detectable watermark. Experimental evaluation has also found that a 32×32 image may be compressed using JPEG by a factor of up to 70 without destruction of the watermark. Such test results are depicted in Table 5. It should be pointed out that for JPEG compression by a factor of 70 results in server distortion of the image, and in fact the image becomes unrecognizable, however, the watermark embedded using the method of the present invention remains detectable in the obscured image. Furthermore, while the present invention was tested using an implementation of JPEG limiting the compression factor to 74, other evaluation techniques project that a watermark embedded using the techniques of the present invention may survive compressions by factors of up to or around 90. Due to the robust nature of the watermarking technique of the present invention, even images that contain texture which allow compression by large factors are likely to retain the watermark even after substantial compression.

TABLE 6

Percentage of correctly identified
watermarking bits for a 256 × 256 image ("Lena")
compressed by JPEG and a filter bank with 4
coefficients.

| JPEG Compression Factor | % Correct Bits |
|---|---|
| 5.23 | 55.9 |
| 7.5 | 51.9 |
| 11.3 | 51.1 |
| 16.7 | 50.1 |

Table 6 depicts tests results that are analogous to those depicted in Table 5, however, the results in Table 6 are for a 256×256 image. Therefore, it is possible to concluded that whatever size or composition an image or data may take, the watermark embedded using the present invention robustly withstands compression techniques that cause the data and primarily images to reach a level of being unrecognizable. Experimentation on the "Lena" image embedded with a watermark using the techniques of the present invention even after decimation by a factor of 20 in each direction, i.e., even when the 256×256 image is reduced to a 12×12 image, retained a recognizable watermark.

TABLE 7

Percentage of correctly identified
watermarking bits for a 256 × 256 image and a filer bank
with 4 coefficients. The image is subject to shrinkage
and zooming.

| JPEG Compression Factor | % Correct Bits |
|---|---|
| 256 | 52.63 |
| 441 | 53.94 |
| 541 | 46.6 |

Such results are summarized in Table 7. When comparing the results of Table 7 with the results of Table 4, it is evident that the watermarking technique of the present invention is more robust to image resizing in larger images than in smaller ones. Experimental results display that decimation of a 64×64 image by the same factor, led to an image size of 3×3, in which both the image and the watermark became unrecognizable.

Those skilled in the art of wavelet processing appreciate that regular wavelets are inherently smooth in their response. Furthermore, the most prominent family of smooth wavelets are the Daubechies wavelets. While smooth wavelets work well in applications such as subband coding, such smooth wavelets or regular wavelets do not perform well for watermarking.

TABLE 8

Percentage of correctly identified
watermarking bits for a 64 × 64 image, compressed by
JPEG, using a Daubechies filter bank with 4
coefficients.

| JPEG Compression Factor | % Correct Bits |
|---|---|
| 7.7 | 65.6 |
| 9.46 | 54.6 |
| 10.53 | 54 |

TABLE 9

Percentage of correctly identified
watermarking bits for a 64 × 64 image, using a
Daubechies filter bank with 4 coefficients. The image
is subjected to shrinkage and zooming.

| Compression Factor | % Correct Bits |
|---|---|
| 1.4 | 54.6 |
| 1.5 | 4x.x(failure) |

Table 8 and 9 support experimentally the fact that such smooth or regular wavelets do not perform well for watermarking. In Table 8, it is shown that watermarking remains robust for JPEG compression, however, watermarking using a regular wavelet cannot survive lowpass filtering and decimation as depicted in Table 9. If a regular wavelet such as a Daubechies wavelet were employed for watermarking, a portion of the watermark would be placed in the low half of the frequencies with another portion of the watermark being placed in the high frequencies. JPEG compression operates by preserving the lowpass frequencies and some highpass components, thus for moderate compression ratios, more than half of the bits in the watermarking sequence can be retrieved. However, after lowpass filtering more than half of the watermark is lost. This result is due to the fact that the Daubechies wavelets do not have the "spread-spectrum capabilities" of the non-regular wavelets of the present invention. The benefit of the present spread-spectrum based technique of the present invention is based on the fact that the watermark is embedded into the signal. In the present invention, it appears that the most prominent non-regular wavelet filters are those related to complimentary sequences.

Multi-Filter Banks

Filter banks and wavelets may be generalized as "multi-filter banks" and "multiwavelets" in which the filters have several inputs and outputs (e.g., multi-filters). For example, two-input two-output filters, for which the matrices have dimensions 2×2, which are here generally known as multi-filters, distinguishing them from a more typical single-input single-output filter or scalar filter. The concept of multi-wavelets is not a straight forward generalization of scalar filter banks and wavelets, since matrix multiplication is generally not commutative.

Figure 10:
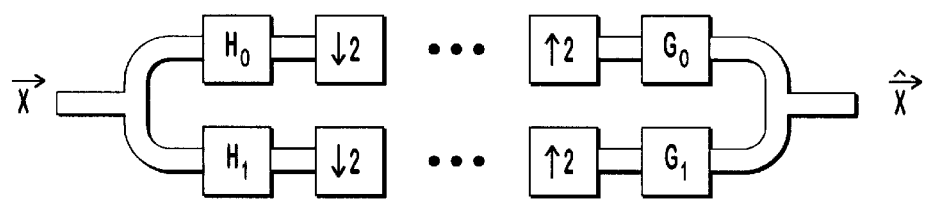
FIG. 10 depicts a simplified diagram of a two-channel vector filter bank, in accordance with an embodiment of the present invention.

In FIG. 10, a two-channel vector filter bank is depicted. The input signal vector $X(z)$ is passed through a bank of two analysis multi-filters, $H_0(z)$ and $H_1(z)$. Following the processing of the multi-filters, each band is then downsampled by a factor of 2. At the receiver end, each band is initially upsampled by inserting a 0 between every two samples to restore the sampling rate. The output of the upsamplers are then passed through a bank of synthesis multi-filters $G_1(z)$ and $G_1(z)$. The resultant vectors are thereafter added together to form $\hat{X}(z)$, which is a replica of the original signal. It should be pointed out that the upsampling and downsampling operations are performed on every component of the vectors separately. The reconstructed signal is:

$$\hat{X}=\tfrac{1}{2}(G_0(z)H_0(z)=G_1(z)H_1(z))X(z)+\tfrac{1}{2}(G_0(z)H_0(-z)+G_1(z)H_1(z))X(-z) \quad (25)$$

To design PR vector filter bank, a solution must be found to the two equations:

$$(G_0(z)H_0(z)+G_1(z)H_1(z))=2I \quad (26)$$

$$(G_0(z)H_1(-z)+G_1(z)H_1(-z))O \quad (27)$$

where the I and O are respectively the unit and zero matrices of appropriate dimensions.

The polyphase decomposition $$H_0(z)=H_{00}(z^2)+Z^{-1}H_{01}(z^2) \qquad (28)$$

In the present multi-filter implementation, orthogonal or paraunitary multi-filter banks are utilized in which the filters for an orthogonal set in $l^2(Z)$:

$$<h_0(n), h_0^T(n+2k)>=\delta_k I \qquad (29)$$

$$<h_1(n), h_1^T(n+2k)>=\delta_k I \qquad (30)$$

$$<h_0(n), h_1^T(n+2k)>=0 \qquad (31)$$

In paraunitary multifilter banks the synthesis filters are given by $$G_0(z)=\hat{H}_0(z) \qquad (32)$$

$$G_1(z)=\hat{H}_1(z). \qquad (33)$$

Note that in general the so-called flip construction $$H_1(z)=\hat{H}_0(-z), \qquad (34)$$

the matrix extension of equation (12), does not work. It can be proven that in orthogonal multifilter banks the flip construction works if and only if $H_0(z)$ is a normal matrix polynomial, i.e. if $H_0(z)$ and $\hat{H}_0(z)$ are commutative [4]. In this embodiment of the present invention, multifilter banks in which $H_0(z)$ is a normal matrix polynomial are employed and thus equation (34) works.

Matrix GRS Sequences and Orthogonal Multifilter Banks

Those skilled in the art of signal processing appreciate that several extensions of the GRS sequences have been proposed for applications such as radar and communication system processing, however, extensions to the matrix case have not been previously proposed. In the present embodiment of the present invention, a new generalization is advanced called "complementary matrix polynomials" or "matrix GRS sequences," wherein two matrix polynomials with coefficients 1 and −1 are called complementary if they satisfy the relationship.

$$A(z)A^T(z^{-1})+B(z)B^T(z^{-1})=C, \qquad (35)$$

where C is a constant matrix.

More generally, C can be allowed to be a unimodular matrix and if such matrix polynomials occur in the diagonal, i.e. the diagonal components are GRS pairs, then they are presently appreciated by those of skill in the art. Therefore, the complimentary matrix polynomials contain all GRS pairs as a special case. Complimentary matrix polynomials are presently presented and were heretofore unknown in the mathematical communication literature. However, because of the attractive properties of their matrix ACF, such complimentary matrix polynomials have inherent merits. For example, one advantage of complimentary polynomials is that the length constraint becomes relaxed. That is to say, while there are no scalar complimentary polynomials with three coefficients, there are pairs of complimentary matrix polynomials where one of the polynomials has three matrix coefficients. Furthermore, the question of the possible lengths of complimentary matrix polynomials remains open for evaluation and is likely difficult to solve. By performing a search, it has been determined that the number of complimentary matrix polynomials considerably exceeds the number of scalar matrix polynomials. Such a discovery provides an additional advantage in enhancing the security of the watermarking process of the present invention.

Another approach at evaluating complimentary matrix polynomials is from the point of view of a multifilter bank. Using such an approach, it is supposed that A(z) and B(z) are two complimentary matrix polynomials. Such a supposition then results in the fact that A(z) and B(z) are the first and second polyphase components of an orthogonal multifilter in a two-channel orthogonal FIR n multifilter bank.

As described above, in the present embodiment of the present invention, commutative multifilter banks are employed. If a multifilter bank is not commutative, i.e. if we assume that $H_0(z)$ has only binary coefficients but is not a normal matrix polynomial, then $H_1(z)$, which forms with $H_0(z)$ a perfect-reconstruction multifilter pair, is not guaranteed to have binary coefficients. Therefore, the design of non-commutative multifilter banks is much more difficult and remains, to a certain extent, an open problem. For the present invention, a preferred implementation for the present embodiment of embedding a watermark, the following perfect-reconstruction multifilter pair may be used:

$$H_0 = \begin{pmatrix} -1-z-z^2-z^3 & -(-1+z+z^2-z^3) \\ -1=z=z^2-z^3 & -1-z-z^2-z^3 \end{pmatrix}, \qquad (36)$$

$$H_1(z)+\hat{H}_0(-z). \qquad (37)$$

Commutativity follows from $$\begin{pmatrix} a & -b \\ b & a \end{pmatrix}\begin{pmatrix} c & -d \\ d & c \end{pmatrix} = \begin{pmatrix} c & -d \\ d & c \end{pmatrix}\begin{pmatrix} a & -b \\ b & a \end{pmatrix} \qquad (38)$$

The polyphase components of (36) are matrix complementary polynomials $$A = \begin{pmatrix} -1-z & 1-z \\ -1+z & -1-z \end{pmatrix}, B = \begin{pmatrix} -1-z-1+z \\ 1-z-1-z \end{pmatrix} \qquad (39)$$

These multifilter banks are highly non-regular and smooth scaling functions and wavelets cannot be obtained. This property is unwelcomed in compression, but is highly desirable in watermarking.

Watermarking Digital Images Using Multifilter Banks

The actual methods for embedding a watermark using multifilter banks is, in principle, similar to the scalar wavelet-based algorithm. The primary difference between the embodiments is that multifilters in the present embodiment replace the scalar filters of the preferred embodiment. The input scalar signal must be split into two signals, e.g. by assigning half of the samples to the first signal and the other half of the samples to the second signal. While such an implementation may be accomplished in several ways, the preferred and simplest approach is to partition the rows or columns into even and odd rows or columns or, alternatively, partitioning into the first half and the second half of rows or columns which results in a vector signal with two components. The vector signal is thereupon subjected to a forward multiwavelet transform with the watermark being embedded using bidirectional coding. The inverse multiwavelet transform is thereafter performed to return the watermarked vector signal. From the watermarked vector signal, a scalar signal is obtained in a way that is the reversal of the procedure with which a vector signal was obtained from the scalar signal above. The output scalar signal results in the desired watermarked version of the input scalar signal.

Detection of the watermark signal embedded using multifilter banks is again, in principle, performed according to the procedure described above relating to scalar transforms. The difference is primarily that prior to the forward wavelet transform, a scalar-to-vector transformation must be used that is exactly the same as the transformation used in the watermarking process.

It should be pointed out that the present embodiment is additionally robust to unauthorized detection since the attacker must additionally discern or guess the scalar-to-vector transformation that has been used which are in addition to the requirements that the attacker must guess the coefficients of the multifilters and the particular form of the subband tree. Experimental results employing the present embodiment demonstrates that the multifilter bank-based technique is additionally more robust to compression and image resizing than the scalar filter bank technique.

TABLE 10

Percentage of correctly identified watermarking bits for a 128 × 128 image, subjected to JPEG compression. The watermarking algorithm is performed using a multifilter bank with 4 matrix coefficients.

| JPEG Compression Factor | % Correct Bits |
| --- | --- |
| 2.94 | 57.8 |
| 4.50 | 53.12 |
| 8.02 | 53.12 |

TABLE 11

Percentage of correctly identified watermarking bits for a 128 × 128 image, subjected to shrinking and zooming. The watermarking algorithm is performed using a multifilter bank with 4 matrix coefficients.

| JPEG Compression Factor | % Correct Bits |
| --- | --- |
| 387 | 54.61 |
| 541 | 50.66 |

Table 10 demonstrates that even after JPEG compression by the maximum compression factor that can be achieved, the watermark embedded using the present invention is still detectable. (Note-as in the previous test results, the quality factor in the JPEG compression scheme was set to the minimum possible, i.e. the actual maximum compression ratio depends on the size of the image and the characteristics of the image.) Additionally, Table 11 depicts the results when a 256×256 image is subjected to shrinking and zooming. By comparing Table 7 with Table 11, the improved performance of the multifilter bank embodiment becomes evident. Such test data comparison demonstrates that using a scalar filter bank in the watermarking process accommodates the detection of the watermark for shrinking the 256×256 image to a size of 12×12 for compression of approximately 441, while in the multifilter bank case, the same image can be shrunk to 11×11 while preserving the watermark.

In conclusion, the present invention presents a novel method for watermarking digital images by employing wavelet transforms. While not all wavelet transforms are suitable for watermarking digital data, e.g. regular wavelets, non-regular filter banks have been disclosed wherein the filters employ binary coefficients. The method of the present invention provides a robust implementation for inserting a watermark and preventing unauthorized detection of the watermark. The watermark embedding process of the present invention embeds the watermark into the data allowing the watermark to be retrievable even if lossy signal processing operations are applied to the watermarked signal. The present invention ensures that the watermark is placed both at high and low frequencies thereby resulting in a strongly resilient watermark even after undergoing lossy compression and image resizing. Experimental results were also presented that support such an implementation. While digital data in the form of digital images were primarily described, the watermarking method of the present invention is applicable without modifications to all media types. Furthermore, the watermarking process of the present invention is additionally suitable for multimedia data combining several forms of media. Furthermore, implementing the present invention using filter coefficients all of which are either 1 or −1 provides additional attractiveness since processing and computation is drastically reduced.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed and desired to be secured by United States Letters Patent is:

1. A method for watermarking digital data, comprising the steps of:
   a) forward transforming said digital data into transformed data using a non-regular wavelet transform having non-continuous functions;
   b) inserting a digital watermark throughout the entire frequency domain on said transformed data; and
   c) inverse transforming said transformed data having said digital watermark embedded therein.

2. The method for watermarking digital data as recited in claim 1, wherein said method further comprises the step of prior to said forward transforming step, partitioning said digital data into blocks such that the amplitude of said digital data within each block exhibits comparable magnitudes.

3. The method for watermarking digital data as recited in claim 1, wherein said forward transforming step further comprises the step of generating a subband tree as a complete subband tree.

4. The method for watermarking digital data as recited in claim 1, wherein said forward transforming step further comprises the step of generating a subband tree that is pruned according to a predetermined pattern.

5. The method for watermarking digital data as recited in claim 1, wherein said forward transforming said digital data into transformed data using a non-regular wavelet transform step, further comprises the step of selecting said non-regular wavelet transform as a orthogonal circular wavelet transform wherein filter coefficients are of the values of either 1 or −1.

6. The method for watermarking digital data as recited in claim 1, wherein said forward transforming said digital data into transformed data using a non-regular wavelet transform step, further comprises the step of selecting said non-regular wavelet transform as a multiwavelet transform wherein filter coefficients are of the values of either 1 or −1.

7. A method for designating and determining the origin of digital data through the use of a digital watermark, comprising the steps of:
   a) generating said digital watermark for uniquely designating said origin of said digital data;
   b) embedding into said digital data said digital watermark throughout the entire frequency domain including the steps of:
      i. forward transforming said digital data into transformed data using a non-regular wavelet transform having non-continuous functions;
      i. inserting said digital watermark on said transformed data; and
      i. inverse transforming said transformed data having said digital watermark embedded therein to form watermarked digital data such that said digital watermark remains resilient to lossy compression of said watermarked digital data; and
   c) upon receipt of unknown digital data, processing said unknown digital data to verify said unknown digital data as being said watermarked digital data having said digital watermark embedded therein.

8. The method for designating and determining the origin of digital data through the use of a digital watermark, as recited in claim 7, wherein said generating step further comprises the step of generating a predetermined pattern for use in pruning a subband tree for said non-regular wavelet transform.

9. The method for designating and determining the origin of digital data through the use of a digital watermark, as recited in claim 7, wherein said forward transforming said digital data into transformed data using said non-regular wavelet transform step, further comprises the step of selecting said non-regular wavelet transform as a orthogonal circular wavelet transform wherein filter coefficients are of the values of either 1 or −1.

10. The method for designating and determining the origin of digital data through the use of a digital watermark, as recited in claim 7, wherein said forward transforming said digital data into transformed data using a non-regular wavelet transform step, further comprises the step of selecting said non-regular wavelet transform as a multiwavelet transform wherein filter coefficients are of the values of either 1 or −1.

11. The method for designating and determining the origin of digital data through the use of a digital watermark, as recited in claim 7, further comprising the step of following said embedding step, lossy compressing said watermarked digital data having said digital watermark embedded therein.

12. The method for designating and determining the origin of digital data through the use of a digital watermark, as recited in claim 11, wherein said lossy compressing step comprises the step of lossy compressing using JPEG compression said watermarked digital data having said digital watermark embedded therein.

13. A method for verifying the origin of digital data, comprising the steps of:
   a) spreading a frequency response of said digital data in a transform domain by forward transforming said digital data with a non-regular circular wavelet transform having non-continuous functions to provide spreading of said digital data to form transformed digital data;
   b) modulating coefficients of said transformed digital data with a digital watermark throughout the entire frequency domain on said transformed data to form watermarked transformed digital data;
   c) despreading said frequency response of said watermarked transformed digital data to form watermarked digital data; and
   d) upon receipt of unknown digital data, determining if said unknown digital data has said digital watermark embedded therein.

14. The method for verifying the origin of digital data, as recited in claim 13, wherein said modulating coefficients of said transformed digital data step comprises the step of inserting said digital watermark onto said coefficients of said transformed digital data.

15. The method for verifying the origin of digital data, as recited in claim 13, wherein said spreading a frequency response step further comprises the step of generating a subband tree that is pruned according to a predetermined pattern.

16. The method for verifying the origin of digital data, as recited in claim 13, further comprising the step of storing for use in said determining step a copy of said digital data and a copy of said digital watermark.

17. The method for verifying the origin of digital data, as recited in claim 16, wherein said determining if said unknown digital data has said digital watermark embedded therein step comprises the steps of:
   a) forward wavelet transforming said watermarked digital data to obtain watermarked digital data coefficients;
   b) forward wavelet transforming said copy of said digital data to obtain digital data coefficients;
   c) comparing a difference between said watermarked digital data coefficients and said digital data coefficients with said copy of said digital watermark; and
   d) when said difference as compared with said copy of said digital watermark is within a verification threshold, detecting said digital watermark within said unknown digital data.

18. A computer-readable medium having computer-executable instructions for designating and determining the origin of digital data through the use of a digital watermark, said computer executable instructions for performing the steps of:
   a) generating said digital watermark for uniquely designating said origin of said digital data;
   b) embedding into said digital data said digital watermark throughout the entire frequency domain including the steps of:
      i. forward transforming said digital data into transformed data using a non-regular wavelet transform having non-continuous functions;
      i. inserting said digital watermark on said transformed data; and
      i. inverse transforming said transformed data having said digital watermark embedded therein to form watermarked digital data such that said digital watermark remains resilient to lossy compression of said watermarked digital data; and
   c) upon receipt of unknown digital data, processing said unknown digital data to verify said unknown digital data as being said watermarked digital data having said digital watermark embedded therein.

19. The computer-readable medium having computer-executable instructions for designating and determining the origin of digital data through the use of a digital watermark, as recited in claim 18, wherein said computer-executable instructions for performing said generating step further comprise computer-executable instructions for performing the step of generating a predetermined pattern for use in pruning a subband tree for said wavelet transform.

20. The computer-readable medium having computer-executable instructions for designating and determining the origin of digital data through the use of a digital watermark, as recited in claim 18, wherein said computer-executable instructions for forward transforming said digital data into transformed data using a non-regular wavelet transform step, further comprise computer-executable instructions for performing the step of selecting said non-regular wavelet transform as a orthogonal circular wavelet transform wherein filter coefficients are of the values of either 1 or −1.

21. The computer-readable medium having computer-executable instructions for designating and determining the origin of digital data through the use of a digital watermark, as recited in claim 18, wherein said computer-executable instructions for forward transforming said digital data into transformed data using a non-regular wavelet transform step, further comprise computer-executable instructions for performing the step of selecting said non-regular wavelet transform as a multiwavelet transform wherein filter coefficients are of the values of either 1 or −1.

22. The computer-readable medium having computer-executable instructions for designating and determining the origin of digital data through the use of a digital watermark, as recited in claim 18, wherein said computer-executable instructions further comprise computer-executable instructions following said embedding step for performing the step of lossy compressing said watermarked digital data having said digital watermark embedded therein.

23. The computer-readable medium having computer-executable instructions for designating and determining the origin of digital data through the use of a digital watermark, as recited in claim 22, wherein said computer-executable instructions for performing said lossy compressing step comprise computer-executable instructions for performing the step of lossy compressing using JPEG compression said watermarked digital data having said digital watermark embedded therein.

* * * * *

UNITED STATES PATENT AND TRADEMARK OFFICE
CERTIFICATE OF CORRECTION

PATENT NO. : 6,359,998 B1
DATED : March 19, 2002
INVENTOR(S) : Todor Cooklev

It is certified that error appears in the above-identified patent and that said Letters Patent is hereby corrected as shown below:

<u>Column 8,</u>
Line 52, before "operation" change "." to -- $\sim$ --

<u>Column 16,</u>
Line 47, change "watcrmarking" to -- watermarking --

<u>Column 18,</u>
Line 66, change the first "$H_1$" to -- $H_0$ --

Signed and Sealed this

Twenty-sixth Day of November, 2002

Attest:

Attesting Officer

JAMES E. ROGAN
Director of the United States Patent and Trademark Office